United States Patent
Mao et al.

(10) Patent No.: US 11,547,288 B2
(45) Date of Patent: Jan. 10, 2023

(54) DEVICE OF ANTI-FOGGING ENDOSCOPE SYSTEM

(71) Applicant: Qingdao O-Mec Medical Technology Co., Ltd., Qingdao (CN)

(72) Inventors: Rongzhuang Mao, Qingdao (CN); Changming Gu, Qingdao (CN); Mingzhi Li, Qingdao (CN)

(73) Assignee: Qingdao O-Mec Medical Technology Co., Ltd., Qingdao (CN)

( * ) Notice: Subject to any disclaimer, the term of this patent is extended or adjusted under 35 U.S.C. 154(b) by 339 days.

(21) Appl. No.: 16/936,313

(22) Filed: Jul. 22, 2020

(65) Prior Publication Data

US 2021/0255456 A1   Aug. 19, 2021

(30) Foreign Application Priority Data

Feb. 17, 2020  (CN) .......................... 202010095217.0

(51) Int. Cl.
*A61B 1/06* (2006.01)
*A61B 1/00* (2006.01)
(Continued)

(52) U.S. Cl.
CPC ........ *A61B 1/0646* (2013.01); *A61B 1/00078* (2013.01); *A61B 1/00121* (2013.01); *A61B 1/00163* (2013.01); *A61B 1/00186* (2013.01); *A61B 1/00188* (2013.01); *A61B 1/018* (2013.01); *A61B 1/04* (2013.01); *A61B 1/05* (2013.01); *A61B 1/0638* (2013.01); *A61B 1/0661* (2013.01); *A61B 1/0684* (2013.01); *A61B 1/127* (2013.01); *G02B 5/208* (2013.01); *G02B 13/14* (2013.01);
(Continued)

(58) Field of Classification Search
CPC ............ A61B 1/00121; A61B 1/00163; A61B 1/00186; A61B 1/04; A61B 1/0638; A61B 1/0661; A61B 1/0684; A61B 1/127
See application file for complete search history.

(56) References Cited

U.S. PATENT DOCUMENTS 5,647,840 A  *  7/1997  D'Amelio ..........  A61B 1/00091
                                                      600/176
6,503,196 B1 *  1/2003  Kehr .................. A61B 1/00135
                                                      600/176
(Continued)

*Primary Examiner* — Aaron B Fairchild
(74) *Attorney, Agent, or Firm* — Dragon Sun Law Firm, PC; Jinggao Li; Nathaniel Perkins

(57) ABSTRACT

This disclosure relates to the minimally invasive medical technical field, and specifically, to a device of anti-fogging endoscope system including a beam of a near-infrared light for anti-fogging, which is coupled into an endoscope imaging optical channel in combination coaxially and is transmitted to the front optical window sheet, the visible light passes through the front optical window sheet, and the near-infrared light is absorbed by the absorption characteristics of the front optical window sheet to raise the temperature of the front optical window sheet. The device is also provided with a cut filter for eliminating the impact on image quality caused by the near-infrared stray light, so that the illumination light source of the prior-art endoscope is not necessary to be changed. It is suitable to integrate the coaxial coupling module with a camera handle or adapter and is more convenient to operate the device.

12 Claims, 1 Drawing Sheet

(51) Int. Cl.
*A61B 1/12* (2006.01)
*G02B 5/20* (2006.01)
*G02B 13/14* (2006.01)
*G02B 27/00* (2006.01)
*G02B 27/14* (2006.01)
*G02B 27/30* (2006.01)
*A61B 1/018* (2006.01)
*A61B 1/05* (2006.01)
*A61B 1/04* (2006.01)

(52) U.S. Cl.
CPC ....... *G02B 27/0006* (2013.01); *G02B 27/141* (2013.01); *G02B 27/30* (2013.01)

(56) References Cited

U.S. PATENT DOCUMENTS

| | | | |
|---|---|---|---|
| 2014/0200406 A1* | 7/2014 | Bennett | A61B 1/128 600/109 |
| 2015/0018613 A1* | 1/2015 | Hollenbeck | A61B 5/6815 600/109 |
| 2015/0173591 A1* | 6/2015 | Zheng | G02B 23/2469 600/169 |

* cited by examiner

DEVICE OF ANTI-FOGGING ENDOSCOPE SYSTEM

CROSS-REFERENCE TO RELATED PATENT APPLICATION

This application claims priority to and the benefit of 202010095217.0, filed Feb. 17, 2020, entitled "Device of anti-fogging endoscope system," by Rongzhuang MAO et al. The entire disclosure of the above-identified application is incorporated herein by reference.

FIELD

This disclosure relates to a minimally invasive medical technical field, and more specifically, to a device of anti-fogging endoscope system.

BACKGROUND

In the minimally invasive surgery using a rigid endoscope system, especially in the laparoscopic surgery, fogging on the protective window at the front end of the endoscope will lead to blurred images due to the temperature difference between the internal and external of the human body and the humid environment inside the human body. The problem has existed for decades, and there are no good solutions to solve the aforementioned problem.

In order to achieve anti-fogging and defogging, the most popular method is to reduce the temperature difference between the front end of the endoscope and the human body, for example, the front-end optical window sheet and the human body. To this end, the electric heating method is used to raise the temperature of the protective window of the endoscope. However, this method has not been widely used, because the product safety cannot be assured when the endoscope is provided with the current.

As a safe way, the light having a predetermined wavelength may be used to irradiate the protective window of the endoscope to raise the temperature for the purpose of anti-fogging or defogging, based on the absorption characteristics of the material of protective window of the endoscope. In the Chinese patent publication No. 201210324982.0 titled "AN ANTI-FOGGING ENDOSCOPE SYSTEM DEVICE AND METHOD", the disclosed device and method using light heating have an effective anti-fogging function, but the image is affected by the surface reflection of the protection window and thus the application is limited.

Therefore, a heretofore unaddressed need exists in the art to address the aforementioned deficiencies and inadequacies.

SUMMARY

Embodiments of the present disclosure provide a device of an anti-fogging endoscope system, so as to solve the technical problem of the image quality degradation. The device of anti-fogging endoscope system comprises a near-infrared light source for anti-fogging on the basis of the traditional endoscope system. A beam of a near-infrared light is coupled into an endoscope imaging optical channel in color combination coaxially, and the near-infrared light is transmitted to the front optical window sheet. The front optical window sheet can allow the visible light to pass through, so as to provide the white light illumination to a surgical field. However, the near-infrared light having a predetermined wavelength band is absorbed by the absorption characteristics of the front optical window sheet. The temperature of the front optical window sheet is raised by the absorbed near-infrared light, and thus the temperature difference between the front optical window sheet of the endoscope and the human body can be reduced. Furthermore, a cut filter is arranged in the front of an image sensor to eliminate the effect of the near-infrared stray light to image quality.

The technical solution of the embodiments of the present disclosure will now be described in detail.

A device of anti-fogging endoscope system comprises a rigid endoscope, an adapter optical system and an image sensor. The rigid endoscope comprises a front optical window sheet and an endoscope optical system, and an imaging wavelength range of the endoscope optical system and an imaging wavelength range of the adapter optical system are from $\lambda 1$ to $\lambda 2$ where $\lambda 2$ is more than $\lambda 1$.

An optical axis of the endoscope optical system is coaxial with an optical axis of the adapter optical system, and the front optical window sheet contains optical materials that allow light having the wavelength range of $\lambda 1 \sim \lambda 2$ to transmit through and absorbs a near-infrared light of a predetermined wavelength band.

The device further comprises a coaxial coupling module and a cut filter, and the coaxial coupling module comprises a semiconductor light source, a collimating lens group and a dichroic mirror.

The semiconductor light source is used to emit the near-infrared light with a wavelength range of $\lambda 3 \sim \lambda 4$, where $\lambda 4$ is more than $\lambda 3$ and $\lambda 3$ is more than $\lambda 2$.

The collimating lens group is used to converge the near-infrared light, and a light emitting surface of the semiconductor light source is located near a focal plane of the collimating lens group.

The dichroic mirror comprises an illumination incident surface, a dichroic plane, an imaging incident surface and an imaging exit surface.

The illumination incident surface is an incident surface on which the near-infrared light for anti-fogging is transmitted to the dichroic mirror, the dichroic plane is used as a transmission plane of an imaging beam of the endoscope system and a reflecting plane of the near-infrared light. The imaging incident surface is an incident surface of the imaging beam of the endoscope system on the coaxial coupling module, and the imaging exit surface is an exit surface of the imaging beam of the endoscope system on the coaxial coupling module.

An optical axis Z1 is a line connecting a center of the illumination incident surface to a center of the dichroic plane and is an incident optical axis of the near-infrared light on the dichroic mirror.

An optical axis Z2 is a line connecting a center of the imaging incident surface to a center of the dichroic plane and is an incident optical axis of the imaging beam of the endoscope system on the coaxial coupling module.

An optical axis Z3 is a line connecting a center of the imaging beam of the endoscope system after the imaging beam of the endoscope system passes through the dichroic plane to a center of the imaging exit surface, and is an exit optical axis of the imaging beam on the coaxial coupling module.

The imaging incident surface and the imaging exit surface are parallel to each other, and are vertical to the illumination incident surface.

The dichroic plane is arranged at an angle of 45° with respect to the illumination incident surface.

The dichroic plane is coated with a dichroic film which reflects the light having wavelength range of $\lambda 3 \sim \lambda 4$ and transmits the light having wavelength range of $\lambda 1 \sim \lambda 2$, and a direction of the reflected light is toward the imaging incident surface.

The optical axis Z1 coincides with an optical axis of the collimating lens group.

The coaxial coupling module is located between the endoscope optical system and the adapter optical system or between the adapter optical system and the image sensor. The optical axis Z2 coincides with an optical axis of the optical system located in front of the coaxial coupling module. The optical axis Z3 coincides with an optical axis of the optical system located behind the coaxial coupling module.

The cut filter is a filter that allows the light with the wavelength range of $\lambda 1 \sim \lambda 2$ to transmit and cuts off the light with the wavelength range of $\lambda 3 \sim \lambda 4$. The cut filter is located behind the coaxial coupling module and in front of the image sensor.

The front optical window sheet has an absorption rate that is more than 10% with respect to the wavelength range of $\lambda 3 \sim \lambda 4$, and optical parts of the endoscope optical system and the adapter optical system are coated with an anti-reflection film with respect to the wavelength range of $\lambda 1 \sim \lambda 2$.

Further, the semiconductor light source is an LED light source, an LD light source or a VCSEL light source, and an emitted light power of the semiconductor light source is more than or equal to 1 W.

Further, the dichroic mirror is a glued prism or a plane dichroic mirror.

Further, a transmittance of the cut filter is less than 0.001% with respect to the wavelength range of $\lambda 3 \sim \lambda 4$.

In the aspects of embodiments of the present disclosure, the near-infrared light for heating is coaxially coupled in the imaging channel, which can solve the problem of the image quality degradation caused by the white light surface reflection due to the near-infrared light transmitted in the illumination channel. Furthermore, it is not necessary to change the illumination light source of the endoscope, it is suitable to integrate the coaxial coupling module with the camera handle or adapter, and thus the operation of the device is more convenient.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION

Figure 1:
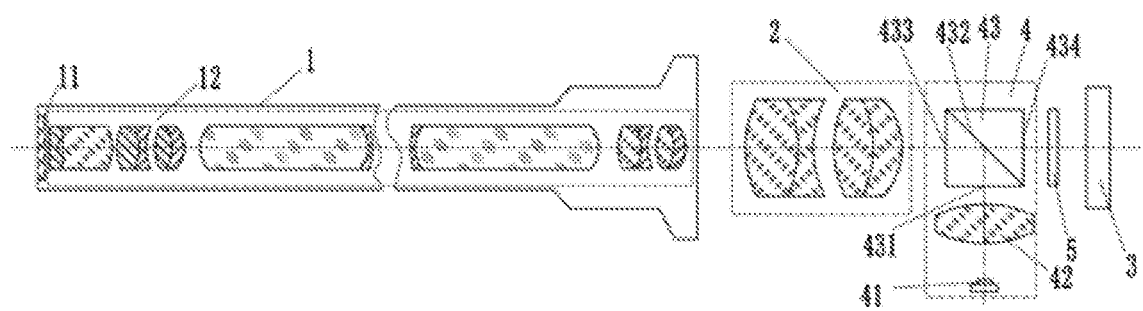
FIG. 1 is a schematic structural view of the device of anti-fogging endoscope system according to one embodiment of the disclosure.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

Figure 2:
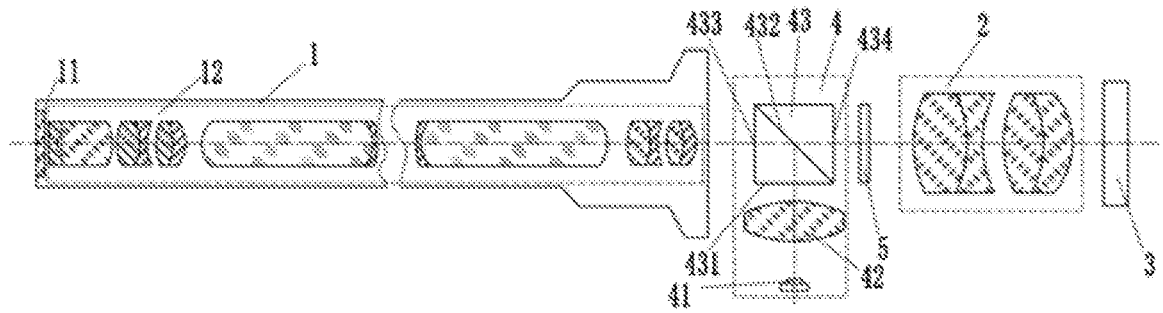
FIG. 2 is a schematic structural view of the device of anti-fogging endoscope system according to the other embodiment of the disclosure.

As shown in FIGS. 1 and 2, a device of anti-fogging endoscope system comprises a rigid endoscope 1, an adapter optical system 2 and an image sensor 3. The rigid endoscope 1 comprises a front optical window sheet 11 and an endoscope optical system 12, and an imaging wavelength range of the endoscope optical system 12 and an imaging wavelength range of the adapter optical system 2 are from $\lambda 1$ to $\lambda 2$ where $\lambda 2$ is more than $\lambda 1$.

An optical axis of the endoscope optical system 12 is coaxial with an optical axis of the adapter optical system 2, and the front optical window sheet 11 contains optical materials that allow light having the wavelength range of $\lambda 1 \sim \lambda 2$ to transmit through and absorbs a near-infrared light of a predetermined wavelength band.

The device further comprises a coaxial coupling module 4 and a cut filter 5, and the coaxial coupling module 4 comprises a semiconductor light source 41, a collimating lens group 42 and a dichroic mirror 43.

The semiconductor light source 41 is used to emit the near-infrared light with a wavelength range of $\lambda 3 \sim \lambda 4$ where $\lambda 4$ is more than $\lambda 3$ and $\lambda 3$ is more than $\lambda 2$.

The collimating lens group 42 is used to converge the near-infrared light, and a light emitting surface of the semiconductor light source 41 is located near a focal plane of the collimating lens group 42.

The dichroic mirror 43 comprises an illumination incident surface 431, a dichroic plane 432, an imaging incident surface 433 and an imaging exit surface 434.

The illumination incident surface 431 is an incident surface on which the near-infrared light for anti-fogging is transmitted to the dichroic mirror 43. The dichroic plane 432 is used as a transmission plane of an imaging beam of the endoscope system and a reflecting plane of the near-infrared light. The imaging incident surface 433 is an incident surface of the imaging beam of the endoscope system on the coaxial coupling module 4, and the imaging exit surface 434 is an exit surface of the imaging beam of the endoscope system on the coaxial coupling module 4.

An optical axis Z1 is a line connecting a center of the illumination incident surface 431 to a center of the dichroic plane 432 and is an incident optical axis of the near-infrared light on the dichroic mirror 43.

An optical axis Z2 is a line connecting a center of the imaging incident surface 433 to a center of the dichroic plane 432 and is an incident optical axis of the imaging beam of the endoscope system on the coaxial coupling module 4.

An optical axis Z3 is a line connecting a center of the dichroic plane 432 from which the imaging beam of the endoscope system is transmitted to a center of the imaging exit surface 434, and is an exit optical axis of the imaging beam on the coaxial coupling module 4.

The imaging incident surface 433 and the imaging exit surface 434 are parallel to each other, and are vertical to the illumination incident surface 431.

The dichroic plane 432 is arranged at an angle of 45° with respect to the illumination incident surface 431.

The dichroic plane 432 is coated with a dichroic film which reflects the light having wavelength range of $\lambda 3 \sim \lambda 4$ and transmits the light having wavelength range of $\lambda 1 \sim \lambda 2$, and a direction of the reflected light is toward the imaging incident surface 433.

The optical axis Z1 coincides with an optical axis of the collimating lens group 42.

The coaxial coupling module 4 is located between the endoscope optical system 12 and the adapter optical system 2 or between the adapter optical system 2 and the image sensor 3. The optical axis Z2 coincides with an optical axis of the optical system located in front of the coaxial coupling module 4. The optical axis Z3 coincides with an optical axis of the optical system located behind the coaxial coupling module 4.

The cut filter 5 is a filter that allows the light with the wavelength range of λ1~λ2 to transmit and cuts off the light with the wavelength range of λ3~λ3. The cut filter 5 is located behind the coaxial coupling module 4 and in front of the image sensor 3.

The front optical window sheet 11 has an absorption rate that is more than 10% with respect to the wavelength range of λ3~λ4. Optical parts of the endoscope optical system 12 and the adapter optical system 2 are coated with an anti-reflection film with respect to the wavelength range of λ1~λ2.

The semiconductor light source 41 is an LED light source, an LD light source or a VCSEL light source. An emitted light power of the semiconductor light source is more than or equal to 1 W.

The dichroic mirror 43 is a glued prism or a plane dichroic mirror.

A transmittance of the cut filter 5 is less than 0.001% with respect to the wavelength range of λ3~λ4.

First Embodiment as Shown FIG. 1

This embodiment has the same structure as mentioned above. Only key data are listed for purposes of clarity.

The semiconductor light source 41 is an LD light source of which a wavelength range is from 805 nm to 810 nm and an emitted light power is 1 W.

The absorption rate of the front optical window sheet 11 is more than 20% in the wavelength range of 805 nm~810 nm.

The imaging wavelength range of the endoscope optical system 12 and the imaging wavelength range of the adapter optical system 2 are from 400 nm to 700 nm. The optical parts of the endoscope optical system 12 and the adapter optical system 2 are coated with the anti-reflection film in the wavelength range from 400 nm to 810 nm.

The dichroic mirror 43 is a glued prism, and the dichroic film of the dichroic plane 432 reflects the light with the wavelength range of 805 nm~810 nm and allows the light with the wavelength range of 400 nm~700 nm to transmit.

The coaxial coupling module 4 is located between the adapter optical system 2 and the image sensor 3.

The cut filter 5 allows the light with the wavelength range from 400 nm to 700 nm to transmit. A transmittance of the cut filter is less than 0.001% in the wavelength range of 805 nm~810 nm. The cut filter 5 is located between the coaxial coupling module 4 and the image sensor 3.

The principle of the disclosure is described as follows.

The near-infrared light with a wavelength of 805 nm~810 nm emitted by the LD light source passes through the collimating lens group 42 to form a slightly scattered light beam. The degree of scatter is the same as the degree of convergence after the near-infrared light passes through the adapter optical system 2 in the endoscope imaging system. The light beam transmits to the dichroic plane 432, exits from the imaging incident surface 433 after reflected, and then enters into the adapter optical system 2. According to the reversibility principle of an optical path, the near-infrared light beam will be irradiated on the front optical window sheet 11 after passing through the adapter optical system 2 and the endoscope optical system 12. Assuming the power of the near-infrared light is 1 W, the near-infrared light of 0.5 W will arrive at the front optical window sheet 11 according to the experimental testing. The temperature of the front optical window sheet 11 is raised by heat generated by the near-infrared light absorption. The temperature of the front optical window sheet 11 can be raised from room temperature of 20° C. to 37° C. within 1 minute according to the experimental testing. At this time, when the endoscope is inserted into the human body, the endoscope is not fogged. A light beam having a wavelength range of 400 nm~700 nm used for imaging passes through the endoscope optical system 12, the adapter optical system 2 and the imaging incident surface 433, and then transmits to the dichroic plane 432. The light beam will pass through the dichroic plane 432 by the existing of the dichroic film, and then transmit to the cut filter 5 through the imaging exit surface 434. Since the cut filter 5 transmits the light having the wavelength range of 400 nm~700 nm, the imaging beam will finally be converged on the image sensor 3 to complete the imaging of the endoscope system. Since the cut filter 5 is provided in front of the image sensor 3 to cut off the wavelength band of 805 nm~810 nm, even if the near-infrared light emitted by the LD light source transmits to the endoscope optical system and the adapter optical system due to the surface reflection, the near-infrared light cannot arrive at the image sensor 3. Therefore, the imaging quality will not be reduced.

Second Embodiment as Shown FIG. 2

This embodiment has the same structure as mentioned above. Only key data are listed for purposes of clarity.

The semiconductor light source 41 is a VCSEL light source of which a wavelength range is from 935 nm to 945 nm and an emitted light power is 2 W.

The absorption rate of the front optical window sheet 11 is 10% in the wavelength range of 935 nm~945 nm.

The imaging wavelength range of the endoscope optical system 12 and the imaging wavelength range of the adapter optical system 2 are from 400 nm to 900 nm. The optical parts of the endoscope optical system 12 and the adapter optical system 2 are coated with the anti-reflection film in the wavelength range from 400 nm to 945 nm.

The dichroic mirror 43 is a glued prism, and the dichroic film of the dichroic plane 432 reflects the light with the wavelength range of 935 nm~945 nm and allows the light with the wavelength range of 400 nm~900 nm to transmit.

The coaxial coupling module 4 is located between the adapter optical system 2 and the image sensor 3.

The cut filter 5 allows the light with the wavelength range from 400 nm to 900 nm to transmit, a transmittance of the cut filter is less than 0.001% in the wavelength range of 935 nm~945 nm, and the cut filter 5 is located between the coaxial coupling module 4 and the image sensor 3.

The principle of this embodiment of the disclosure is similar to that of first embodiment, and thus will be omitted here.

The technical solution of the present disclosure is particularly suitable for application in an endoscope system to realize the anti-fogging function.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An anti-fogging endoscope system device, comprising a rigid endoscope, an adapter optical system and an image sensor, wherein the rigid endoscope comprises a front optical window sheet and an endoscope optical system, and an imaging wavelength range of the endoscope optical system and an imaging wavelength range of the adapter optical system are from $\lambda 1$ to $\lambda 2$ where $\lambda 2$ is more than $\lambda 1$;

an optical axis of the endoscope optical system is coaxial with an optical axis of the adapter optical system and the front optical window sheet contains optical materials that allow light having the wavelength range of $\lambda 1 \sim \lambda 2$ to transmit through and absorbs a near-infrared light of a predetermined wavelength band;

the device further comprises a coaxial coupling module and a cut filter, and the coaxial coupling module comprises a semiconductor light source, a collimating lens group and a dichroic mirror;

the semiconductor light source is used to emit the near-infrared light with a wavelength range of $\lambda 3 \sim \lambda 4$ where $\lambda 4$ is more than $\lambda 3$ and $\lambda 3$ is more than $\lambda 2$;

the collimating lens group is used to converge the near-infrared light, and a light emitting surface of the semiconductor light source is located near a focal plane of the collimating lens group;

the dichroic mirror comprises an illumination incident surface, a dichroic plane, an imaging incident surface and an imaging exit surface;

the illumination incident surface is an incident surface on which the near-infrared light for anti-fogging is transmitted to the dichroic mirror, the dichroic plane is used as a transmission plane of an imaging beam of the endoscope system and a reflecting plane of the near-infrared light, the imaging incident surface is an incident surface of the imaging beam of the endoscope system on the coaxial coupling module, and the imaging exit surface is an exit surface of the imaging beam of the endoscope system on the coaxial coupling module;

an optical axis Z1 is a line connecting a center of the illumination incident surface and a center of the dichroic plane and is an incident optical axis of the near-infrared light on the dichroic mirror;

an optical axis Z2 is a line connecting a center of the imaging incident surface and a center of the dichroic plane and is an incident optical axis of the imaging beam of the endoscope system on the coaxial coupling module;

an optical axis Z3 is a line connecting a center of the dichroic plane from which the imaging beam of the endoscope system is transmitted and a center of the imaging exit surface, and is an exit optical axis of the imaging beam on the coaxial coupling module;

the imaging incident surface and the imaging exit surface are parallel to each other, and are perpendicular to the illumination incident surface;

the dichroic plane is arranged at an angle of 45° with respect to the illumination incident surface;

the dichroic plane is coated with a dichroic film which reflects the light having wavelength range of $\lambda 3 \sim \lambda 4$ and transmits the light having wavelength range of $\lambda 1 \sim \lambda 2$, and a direction of the reflected light is toward the imaging incident surface;

the optical axis Z1 coincides with an optical axis of the collimating lens group;

the coaxial coupling module is located between the endoscope optical system and the adapter optical system or between the adapter optical system and the image sensor, the optical axis Z2 coincides with an optical axis of the optical system located in front of the coaxial coupling module, and the optical axis Z3 coincides with an optical axis of the optical system located behind the coaxial coupling module;

the cut filter is a filter that allows the light with the wavelength range of $\lambda 1 \sim \lambda 2$ to transmit and cuts off the light with the wavelength range of $\lambda 3 \sim \lambda 4$, the cut filter is located behind the coaxial coupling module and in front of the image sensor; and the front optical window sheet has an absorption rate that is more than 10% with respect to the wavelength range of $\lambda 3 \sim \lambda 4$, and optical parts of the endoscope optical system and the adapter optical system are coated with an anti-reflection film with respect to the wavelength range of $\lambda 1 \sim \lambda 2$.

2. The device as claimed in claim 1, wherein the semiconductor light source is a LED light source, an LD light source or a VCSEL light source, and an emitted light power of the semiconductor light source is more than or equal to 1 W.

3. The device as claimed in claim 2, wherein the semiconductor light source is the LD light source of which a wavelength range is from 805 nm to 810 nm and the emitted light power is 1 W;

the absorption rate of the front optical window sheet is more than 20% in the wavelength range of 805 nm~810 nm;

the imaging wavelength range of the endoscope optical system and the imaging wavelength range of the adapter optical system are from 400 nm to 700 nm, and the optical parts of the endoscope optical system and the adapter optical system are coated with the anti-reflection film in the wavelength range from 400 nm to 810 nm;

the dichroic mirror is a glued prism, and the dichroic film of the dichroic plane reflects the light with the wavelength range of 805 nm~810 nm and allows the light with the wavelength range of 400 nm~700 nm to transmit;

the coaxial coupling module is located between the adapter optical system and the image sensor; and the cut filter allows the light with the wavelength range from 400 nm to 700 nm to transmit, a transmittance of the cut filter is less than 0.001% in the wavelength range of 805 nm~810 nm, and the cut filter is located between the coaxial coupling module and the image sensor.

4. The device as claimed in claim 2, wherein the semiconductor light source is the VCSEL light source of which the wavelength range is from 935 nm to 945 nm and the emitted light power is 2 W;
the absorption rate of the front optical window sheet is 10% in the wavelength range of 935 nm~945 nm;
the imaging wavelength range of the endoscope optical system and the imaging wavelength range of the adapter optical system are from 400 nm to 900 nm, and the optical parts of the endoscope optical system and the adapter optical system are coated with the anti-reflection film in the wavelength range from 400 nm to 945 nm;
the dichroic mirror is a glued prism, and the dichroic film of the dichroic plane reflects the light with the wavelength range of 935 nm~945 nm and allows the light with the wavelength range of 400 nm~900 nm to transmit;
the coaxial coupling module is located between the adapter optical system and the image sensor; and
the cut filter allows the light with the wavelength range from 400 nm to 900 nm to transmit, a transmittance of the cut filter is less than 0.001% in the wavelength range of 935 nm~945 nm, and the cut filter is located between the coaxial coupling module and the image sensor.

5. The device as claimed in claim 1, wherein the dichroic mirror is a glued prism or a plane dichroic mirror.

6. The device as claimed in claim 5, wherein the semiconductor light source is an LD light source of which a wavelength range is from 805 nm to 810 nm and an emitted light power is 1 W;
the absorption rate of the front optical window sheet is more than 20% in the wavelength range of 805 nm~810 nm;
the imaging wavelength range of the endoscope optical system and the imaging wavelength range of the adapter optical system are from 400 nm to 700 nm, and the optical parts of the endoscope optical system and the adapter optical system are coated with the anti-reflection film in the wavelength range from 400 nm to 810 nm;
the dichroic mirror is the plane dichroic mirror, and the dichroic film of the dichroic plane reflects the light with the wavelength range of 805 nm~810 nm and allows the light with the wavelength range of 400 nm~700 nm to transmit;
the coaxial coupling module is located between the adapter optical system and the image sensor; and
the cut filter allows the light with the wavelength range from 400 nm to 700 nm to transmit, a transmittance of the cut filter is less than 0.001% in the wavelength range of 805 nm~810 nm, and the cut filter is located between the coaxial coupling module and the image sensor.

7. The device as claimed in claim 5, wherein the semiconductor light source is a VCSEL light source of which a wavelength range is from 935 nm to 945 nm and an emitted light power is 2 W;
the absorption rate of the front optical window sheet is 10% in the wavelength range of 935 nm~945 nm;
the imaging wavelength range of the endoscope optical system and the imaging wavelength range of the adapter optical system are from 400 nm to 900 nm, and the optical parts of the endoscope optical system and the adapter optical system are coated with the anti-reflection film in the wavelength range from 400 nm to 945 nm;
the dichroic mirror is the plane dichroic mirror, and the dichroic film of the dichroic plane reflects the light with the wavelength range of 935 nm~945 nm and allows the light with the wavelength range of 400 nm~900 nm to transmit;
the coaxial coupling module is located between the adapter optical system and the image sensor; and
the cut filter allows the light with the wavelength range from 400 nm to 900 nm to transmit, a transmittance of the cut filter is less than 0.001% in the wavelength range of 935 nm~945 nm, and the cut filter is located between the coaxial coupling module and the image sensor.

8. The device as claimed in claim 1, wherein a transmittance of the cut filter is less than 0.001% with respect to the wavelength range of $\lambda 3$~$\lambda 4$.

9. The device as claimed in claim 8, wherein the semiconductor light source is an LD light source of which a wavelength range is from 805 nm to 810 nm and an emitted light power is 1 W;
the absorption rate of the front optical window sheet is more than 20% in the wavelength range of 805 nm~810 nm;
the imaging wavelength range of the endoscope optical system and the imaging wavelength range of the adapter optical system are from 400 nm to 700 nm, and the optical parts of the endoscope optical system and the adapter optical system are coated with the anti-reflection film in the wavelength range from 400 nm to 810 nm;
the dichroic mirror is a plane dichroic mirror, and the dichroic film of the dichroic plane reflects the light with the wavelength range of 805 nm~810 nm and allows the light with the wavelength range of 400 nm~700 nm to transmit;
the coaxial coupling module is located between the adapter optical system and the image sensor; and
the cut filter allows the light with the wavelength range from 400 nm to 700 nm to transmit, the transmittance of the cut filter is less than 0.001% in the wavelength range of 805 nm~810 nm, and the cut filter is located between the coaxial coupling module and the image sensor.

10. The device as claimed in claim 8, wherein the semiconductor light source is a VCSEL light source of which a wavelength range is from 935 nm to 945 nm and an emitted light power is 2 W;
the absorption rate of the front optical window sheet is 10% in the wavelength range of 935 nm~945 nm;
the imaging wavelength range of the endoscope optical system and the imaging wavelength range of the adapter optical system are from 400 nm to 900 nm, and the optical parts of the endoscope optical system and the adapter optical system are coated with the anti-reflection film in the wavelength range from 400 nm to 945 nm;
the dichroic mirror is a plane dichroic mirror, and the dichroic film of the dichroic plane reflects the light with the wavelength range of 935 nm~945 nm and allows the light with the wavelength range of 400 nm~900 nm to transmit;
the coaxial coupling module is located between the adapter optical system and the image sensor; and the cut filter allows the light with the wavelength range from 400 nm to 900 nm to transmit, the transmittance of the cut filter is less than 0.001% in the wavelength range of 935 nm~945 nm, and the cut filter is located between the coaxial coupling module and the image sensor.

11. The device as claimed in claim 1, wherein the semiconductor light source is an LD light source of which a wavelength range is from 805 nm to 810 nm and an emitted light power is 1 W;
- the absorption rate of the front optical window sheet is more than 20% in the wavelength range of 805 nm~810 nm;
- the imaging wavelength range of the endoscope optical system and the imaging wavelength range of the adapter optical system are from 400 nm to 700 nm, and the optical parts of the endoscope optical system and the adapter optical system are coated with the anti-reflection film in the wavelength range from 400 nm to 810 nm;
- the dichroic mirror is a glued prism, and the dichroic film of the dichroic plane reflects the light with the wavelength range of 805 nm~810 nm and allows the light with the wavelength range of 400 nm~700 nm to transmit;
- the coaxial coupling module is located between the adapter optical system and the image sensor; and
- the cut filter allows the light with the wavelength range from 400 nm to 700 nm to transmit, a transmittance of the cut filter is less than 0.001% in the wavelength range of 805 nm~810 nm, and the cut filter is located between the coaxial coupling module and the image sensor.

12. The device as claimed in claim 1, wherein the semiconductor light source is a VCSEL light source of which a wavelength range is from 935 nm to 945 nm and an emitted light power is 2 W;
- the absorption rate of the front optical window sheet is 10% in the wavelength range of 935 nm~945 nm;
- the imaging wavelength range of the endoscope optical system and the imaging wavelength range of the adapter optical system are from 400 nm to 900 nm, and the optical parts of the endoscope optical system and the adapter optical system are coated with the anti-reflection film in the wavelength range from 400 nm to 945 nm;
- the dichroic mirror is a glued prism, and the dichroic film of the dichroic plane reflects the light with the wavelength range of 935 nm~945 nm and allows the light with the wavelength range of 400 nm~900 nm to transmit;
- the coaxial coupling module is located between the adapter optical system and the image sensor; and
- the cut filter allows the light with the wavelength range from 400 nm to 900 nm to transmit, a transmittance of the cut filter is less than 0.001% in the wavelength range of 935 nm~945 nm, and the cut filter is located between the coaxial coupling module and the image sensor.

* * * * *